United States Patent

Mulhall

Patent Number: 5,280,094
Date of Patent: Jan. 18, 1994

[54] BIS (DIALLYLAMINO) SILANES

[75] Inventor: Steven E. Mulhall, Monroeville Boro, Pa.

[73] Assignee: Aristech Chemical Corporation, Pittsburgh, Pa.

[21] Appl. No.: 16,228

[22] Filed: Feb. 11, 1993

Related U.S. Application Data

[63] Continuation of Ser. No. 965,320, Oct. 23, 1992, abandoned, which is a continuation-in-part of Ser. No. 894,970, Jun. 8, 1992, abandoned.

[51] Int. Cl.$^5$ .................... C08F 230/08; C08F 210/00
[52] U.S. Cl. ...................................... 526/279; 526/348
[58] Field of Search ........................................ 526/279

[56] References Cited

U.S. PATENT DOCUMENTS 3,445,387  5/1969  Liston ................................ 252/32.7

FOREIGN PATENT DOCUMENTS 0423438  4/1991  European Pat. Off. .

OTHER PUBLICATIONS

Giannini et al, Stereospecific Polymerization of Monomers Containing Oxygen and Nitrogen with Ziegler-Natta Catalysts, Polymer Letters, vol. 5, pp. 527-533, (1967).

Gianni et al, Polymerization of Nitrogen-Containing and Oxygen-Containing Monomers by Ziegler-Natta Catalysts, J. Polymer Sci.:Part C22, pp. 157-175, (1968).

Primary Examiner—Joseph L. Schofer
Assistant Examiner—Wu C. Cheng
Attorney, Agent, or Firm—William L. Krayer

[57] ABSTRACT

Bis(diallylamino) silanes of the formula

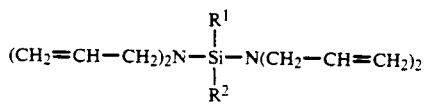

where $R^1$ and $R^2$ are lower alkyl or phenyl groups are copolymerized with lower olefins and desilylated to exhibit amine functionality; they are receptive to dyes.

4 Claims, No Drawings

BIS (DIALLYLAMINO) SILANES

This is a continuation of application Ser. No. 965,320, filed Oct. 23, 1992 abandoned, which is a continuation-in-part of my co-pending application Ser. No. 894,970, filed Jun. 8, 1992 abandoned.

TECHNICAL FIELD

This invention relates to the use of bis(diallylamino) silanes of the general formula

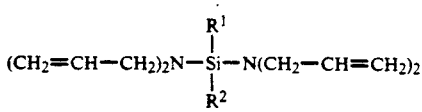

where $R^1$ and $R^2$ are independently selected from alkyl and aryl groups having 1 to 6 carbon atoms as comonomers for lower olefins polymerized in highly active Ziegler-Natta catalyst systems.

BACKGROUND ART

In European Patent Publication 0423438, Sivak et al propose the use of protected diallyl amine monomers for copolymerization with ethylene, propylene, and other lower alpha-olefins having up to 8 carbon atoms. Protection of the otherwise vulnerable amine group is provided by a silyl group having relatively bulky substituents, such as lower alkyl or phenyl groups. Diallyl amines are proposed and several examples are given of silyl-protected diallyl amines. However, bis-diallyl amines are not contemplated.

SUMMARY OF INVENTION

I have invented new compounds of the general formula

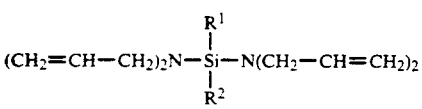

where $R^1$ and $R^2$ are independently selected from alkyl and aryl groups having 1 to 6 carbon atoms. They may be used as cross-linking agents in polymers and find special utility as comonomers for lower olefins polymerized in highly active Ziegler-Natta catalyst systems.

DETAILED DESCRIPTION OF THE INVENTION

My invention will be described with respect to two paradigms, namely bis(diallylamino)dimethylsilane and bis(diallylamino)diphenylsilane.

EXAMPLE I

Bis(diallylamino)dimethylsilane

The equipment used for the synthesis of bis(diallylamino)dimethylsilane was set up in the following manner. A reflux condenser, mechanical stirrer and 125 ml addition funnel were placed on a 2000 ml 3-necked, round-bottomed flask. An argon inlet was connected to the top of the reflux condenser and a heating mantle was placed on the flask. The flask was flushed with argon (allowing the argon to exit the setup through the top of the addition funnel) until the atmosphere in the glassware was assured of being inert.

Heptane (400 ml), triethylamine (136.62 g, 1.350 moles, 188 ml) and diallylamine (98.36 g, 1.012 moles, 125 ml) were charged into the reaction flask. Dichlorodimethylsilane (43.55 g, 0.3375 moles, 41 ml) was placed in the addition funnel and added to the reaction mixture in the flask over a period of 70 minutes. The temperature of the reaction mixture reached 37.5° C. (as measured by a thermocouple between the flask and heating mantle).

The reaction produces a large amount of salts (triethylamine hydrochloride and diallylamine hydrochloride) and twice during the reaction additional heptane had to be added (200 ml portions each time) in order to keep the slurry thinned to a stirrable consistency.

After the addition of dichlorodimethylsilane was complete, the mixture was heated to reflux for five hours. The flask was then allowed to cool to room temperature.

The salts were removed by filtration using a buchner funnel covered with a latex dam to keep exposure to the atmosphere to a minimum. the product was isolated from the filtrate by distillation. The heptane and excess amines were removed at a vacuum of 40 mmHg with a temperature range from ambient to 43° C. The product distilled at 72.6°–74.6° C. at 1 mmHg.

61.2 g of bis(diallylamino)dimethylsilane was isolated by this technique which corresponds to a yield of 72% of theoretical after distillation.

EXAMPLE II

Bis(diallylamino)diphenylsilane

The glassware setup used for the preparation of bis(diallylamino)diphenylsilane was the same as the equipment used for the synthesis of bis(diallylamino)dimethylsilane above except that a 1000 ml flask was used instead of a 2000 ml flask.

After the system was flushed with argon, triethylamine (159.84 g, 1.580 moles, 220.2 ml), diallylamine (84.48 g, 0.8699 moles, 107.3 ml) and toluene (200 ml) were added to the reaction flask. Dichlorodiphenylsilane (100.75 g, 0.3980 moles, 83.7 ml) was charged into the addition funnel and added to the reaction mixture in the flask over a period of 15 minutes, the temperature rose to 600° C.

A large amount of solid precipitated from the mixture. Toluene (100 ml) was added to the flask through the addition funnel to rinse out the remaining silane and make the reaction mixture more stirrable and the mixture was heated to reflux for two hours, then cooled to room temperature.

The salts were removed by filtration using a sealed pressure filter under an inert atmosphere. The product was isolated from the filtrate by distillation. The heptane and excess amines were removed at a vacuum of 40 mmHg with a temperature range from ambient to 430° C. The product distilled in a range from 160°/0.3 mmHg to 160°/0.1 mmHg.

101.5 g of bis(diallylamino)diphenylsilane was isolated by this technique which corresponds to a yield of 68% of theoretical after distillation.

Similar preparations may be made for the diethyl, dipropyl, dibutyl, dipentyl, dihexyl and methylphenyl variants.

My new monomers may be incorporated into chains of crystalline polypropylene and other lower olefin polymers as described in the above-mentioned Sivak et al patent. Thereafter, the silyl groups may be removed by hydrolysis or alcoholysis optionally promoted by acidic or basic catalysis and the remaining copolymers, which may be mildly cross-linked, will exhibit amine functionality or ammonium functionality in the presence of acids.

My monomers may be homopolymerized using Ziegler-Natta systems and/or copolymerized in amounts to yield copolymers having ratios of lower olefin to my monomer (m) of 0.1 mole % to 99.9 mole %.

Following are examples of propylene copolymerizations with bis(diallylamino)dimethylsilane ("BDMS") and bis(diallylamino)diphenylsilane ("BDPS").

General Copolymerization Procedure

Standard inert atmosphere techniques were used to exclude moisture and oxygen throughout the manipulations.

An apparatus consisting of a round bottom flask fitted with a side arm, magnetic stirring bar and a stopper was assembled hot from a drying oven and was then either evacuated and refilled with inert gas several times or (and) purged with inert gas for at least 15 minutes. The flask was charged with a given amount of solvent, heptane or toluene, usually 125 mL. The solvents were freshly distilled from sodium and triethyl-aluminum (TEA) over which they had been refluxed for at least 18 hours under an inert atmosphere.

At this point the inert gas atmosphere in the flask was replaced with the gaseous comonomer by a minimum of three cycles of evacuation and refilling back to atmospheric pressure with the comonomer. After the third cycle the solution was stirred for at least ten minutes (usually longer) to allow the solvent to become saturated with the comonomer. Pressure was maintained at one atmosphere via a bubbler.

Next was added an "external donor", which was diphenyldimethoxysilane. Phenyltrimethoxysilane may alternatively be used. Then the other comonomer was added. A given amount of alkyl aluminum co-catalyst, which was in the form of a heptane solution of about 25% by weight (0.715 g/mL in heptane), was also added to the flask.

The polymerization was initiated by the addition of the transition metal containing co-catalyst, which was a titanium tetrachloride on a magnesium chloride support. At this point the flask was lowered into a was lowered into a thermostated oil bath and magnetic stirring was begun.

An excess of gaseous comonomer was passed into the flask in order to replace any that was consumed. Excess gaseous comonomer was allowed to pass from the reaction vessel via a bubbler, maintaining a pressure in the flask of one atmosphere.

After a specified period of time the reaction was quenched by the addition of acidified alcohol (HCl in iso-propanol, ethanol and/or methanol). The quenched reaction slurry was combined with the alcohol solution of volume at least twice the original volume of the inert reaction solvent. The resultant slurry was stirred for at least 45 minutes and then filtered. This treatment not only stopped the reaction, it dissolved catalyst residues and removed silyl groups and thus regenerated the amino groups.

If the filtration proceeded very slowly, the slurry was combined with enough water to make the filtration proceed at a convenient rate.

The polymer was resuspended in alcohol, stirred, filtered and vacuum dried overnight.

Boiling heptane soluble content was determined by standard methods.

Homopolymerization of propylene under these conditions produces polypropylene with yields in the range of 200–220 g polymer/g titanium-containing catalyst. The extent of reduction in polymer yield in the copolymerizations relative to this homopolymer yield is used as a rough guide to the utility of the comonomers in the copolymerization systems.

Copolymerizations of Propylene with Bis(diallylamino) dimethylsilane (BDMS)

EXAMPLE III

The general copolymerization procedure above was followed using the following quantities of reagents and reaction conditions in the polymerization.

| Solvent | heptane | 100 mL |
|---|---|---|
| External Donor | DPMS | 75 μL |
| Comonomer | BDMS | 3.85 g |
| Cocatalyst | triethylaluminum | 4.3 mL (25 wt %) |
| TiCl4/MgCl2 Catalyst | | 91 mg |
| Reaction Temperature | | 50° C. |
| Reaction Time | | 2 hr |
| Alcohol Used in Work Up | | iso-propanol |

The polymerization yielded 8.3 g of polymer which is a yield of 91.2 g polymer/g catalyst. This corresponds to about 40% of the yield of a homopolymerization of propylene under these conditions.

EXAMPLE IV

This polymerization was done using the following quantities of reagents and reaction conditions with the general copolymerization procedure from above.

| Solvent | heptane | 75 mL |
|---|---|---|
| External Donor | DPMS | 225 μL |
| Comonomer | BDMS | 11.12 g |
| Cocatalyst | triethylaluminum | 12.9 mL (25 wt %) |
| TiCl4/MgCl2 Catalyst | | 104 mg |
| Reaction Temperature | | 50° C. |
| Reaction Time | | 2 hr |
| Alcohol Used in Work Up | | iso-propanol |

Polymer (5.8 g) was produced in this polymerization which is a yield of 55.5 g polymer/g catalyst which is approximately 25% of a comparable homopolymerization.

Copolymerizations of Propylene with Bis(diallylamino) diphenylsilane (BDPS)

EXAMPLE V

The following quantities of reagents and reaction conditions were used with the general copolymerization procedure.

| Solvent | heptane | 100 mL |
|---|---|---|
| External Donor | DPMS | 220 μL |
| Comonomer | BDPS | 18.19 g |
| Cocatalyst | triethylaluminum | 12.5 mL (25 wt %) |
| TiCl4/MgCl2 Catalyst | | 137 mg |
| Reaction Temperature | | 50° C. |
| Reaction Time | | 2 hr |
| Alcohol Used in Work Up | | iso-propanol |

The polymerization yielded 15.4 g of polymer which is a yield of 112.4 g polymer/g catalyst which is in the range of 51–57% of a comparable propylene homopolymerization. 98.4% of a tested sample was insoluble in boiling heptane.

EXAMPLE VI

The following quantities of reagents and reaction conditions were used with the general copolymerization procedure.

| Solvent | heptane. | 50 mL |
|---|---|---|
| External Donor | DPMS | 400 μL |
| Comonomer | BDPS | 31.97 g |
| Cocatalyst | triethylaluminum | 23.5 mL (25 wt %) |
| TiCl4/MgCl2 Catalyst | | 117 mg |
| Reaction Temperature | | 50° C. |
| Reaction Time | | 2 hr |
| Alcohol Used in Work Up | | iso-propanol |

Copolymer (17.0 g) was produced by this copolymerization which corresponds to a yield of 145.3 g polymer/g catalyst. This is about 70% of what is produced in a comparable propylene homopolymerization. The fraction insoluble in boiling heptane was 91.8% of the tested sample.

Uptake of an Acid Dye by Polymer Samples as a Test for Amine Incorporation

EXAMPLE VII

A sample of propylene homopolymer was prepared using the general polymerization conditions given above and used as a blank in the dye uptake experiments described below.

A stock solution of dye was prepared by dissolving Acid Alizarin Blue BB dye (1.00 g) and ammonium acetate (7.0 g) in water to obtain 80 grams of solution.

Samples (200 mg) of the propylene homopolymer and each of the four propylene/amine copolymers produced in Examples 1–4 above were placed in test tubes and 10 mL of the stock dye solution was added. The samples were sealed and shaken to assure dispersion of the polymer powder in the dye and placed in a 60° C. water bath. The temperature of the bath was increased to 100° C. over a period of 30 minutes and held at that temperature for 1 hour and then cooled to room temperature.

The samples were filtered and rinsed repeatedly with water until the rinsings were clear and the color of the powder did not appear to change. The rinsings were then continued with an equivalent amount of water. The total amount of water used was about 500 ml. The samples were then suspended in boiling water for about one minute and then filtered and this hot wash was repeated two more times.

After the samples were dried, their color intensities were compared and are described in Table 1 below.

TABLE 1

| Dyed Propylene/Amine Copolymers | |
|---|---|
| Sample | Color |
| Propylene homopolymer | very pale pink/purple color |
| Example III | slightly more intense purple than propylene homopolymer |
| Example IV | pale purple |
| Example V | pale purple |
| Example VI | reasonably intense purple/blue color |

I claim:

1. A copolymer of about 0.1% to about 99.9% lower alpha-olefin having 2 to 8 carbon atoms and a bis(diallylamino) silane of the formula

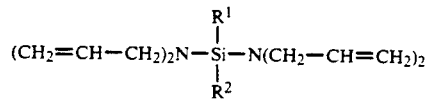

where $R^1$ and $R^2$ are independently selected from alkyl and aryl groups having 1 to 6 carbon atoms.

2. Copolymer of claim 1 wherein the alpha-olefin is propylene.

3. Copolymer of claim 1 wherein the silane is bis(diallylamino) dimethylsilane.

4. Copolymer of claim 1 wherein the silane is bis(diallylamino) diphenylsilane.

* * * * *

UNITED STATES PATENT AND TRADEMARK OFFICE
CERTIFICATE OF CORRECTION

PATENT NO. : 5,280,094

DATED : January 18, 1994

INVENTOR(S) : Steven E. Mulhall

It is certified that error appears in the above-identified patent and that said Letters Patent is hereby corrected as shown below:

Column 2, line 45, change "600°C." to -- 60°C. --;

line 56, change "430°" to -- 43° --.

Column 3, lines 46 and 47, after "was lowered into a" delete

-- was lowered into a --, second occurrence.

Signed and Sealed this

Twenty-fourth Day of May, 1994

Attest:

BRUCE LEHMAN

*Attesting Officer*    *Commissioner of Patents and Trademarks*